United States Patent

Baumgart et al.

[11] Patent Number: 5,263,955
[45] Date of Patent: Nov. 23, 1993

[54] MEDULLARY NAIL

[76] Inventors: Rainer Baumgart, Athener Platz 11, 8000 Munich 90; Augustin Betz, Am Sonnengrund 4a, 8130 Starnberg, both of Fed. Rep. of Germany

[21] Appl. No.: 655,445
[22] PCT Filed: Jul. 4, 1990
[86] PCT No.: PCT/EP90/01076
 § 371 Date: Mar. 4, 1991
 § 102(e) Date: Mar. 4, 1991
[87] PCT Pub. No.: WO91/00065
 PCT Pub. Date: Jan. 10, 1991

[30] Foreign Application Priority Data
 Jul. 4, 1989 [DE] Fed. Rep. of Germany ....... 3921972

[51] Int. Cl.⁵ .............................................. A61B 17/56
[52] U.S. Cl. ........................................ 606/63; 606/64; 606/62
[58] Field of Search ....................... 606/60, 62, 63, 64, 606/68, 72, 73, 96, 104, 105

[56] References Cited
U.S. PATENT DOCUMENTS

| 4,227,518 | 10/1980 | Aginsky | 606/63 |
| 4,858,602 | 8/1989 | Seidel et al. | 606/64 X |
| 4,875,475 | 10/1989 | Comte et al. | 606/64 |
| 5,074,882 | 12/1991 | Grammont et al. | 606/63 X |

FOREIGN PATENT DOCUMENTS

| 2213283 | 8/1973 | Fed. Rep. of Germany . |
| 2417233 | 10/1975 | Fed. Rep. of Germany . |
| 2802404 | 1/1978 | Fed. Rep. of Germany . |
| 3541597 | 11/1985 | Fed. Rep. of Germany . |
| 2224214 | 11/1989 | Fed. Rep. of Germany . |
| 8907561.7 | 11/1989 | Fed. Rep. of Germany . |
| 2267080 | 11/1975 | France . |
| 2338685 | 8/1977 | France . |

OTHER PUBLICATIONS

International Search Report of application PCT/EP 90/01076 dated Jun. 12, 1990 (4 pgs.).
Office Action relating to the German Priority Application P 39 21 972.0, dated Jun. 3, 1990 (2 pgs.).

*Primary Examiner*—Robert A. Hafer
*Assistant Examiner*—Brian E. Hanlon
*Attorney, Agent, or Firm*—John F. A. Earley; John F. A. Earley, III

[57] ABSTRACT

A medullary nail (10) has a cavity (12) in which an inner part (20) can slide longitudinally without being able to rotate. The wall (11) of the medullary nail (10) which forms the cavity (12) is traversed on opposite sides by an elongated hole (16) in the region of the driving-in end (14). At least one fastening hole (22) aligned flush with the elongated hole (16) is provided in the inner part (20). When the connecting screws are driven into the spaced fastening holes (15, 16, 22) and an osteotomy is located between the connecting screws (15, 22), the edges of the osteotomy are moved apart as the inner part slides longitudinally, and the slowly widening gap between the edges of the osteotomy becomes filled with bone tissue.

8 Claims, 3 Drawing Sheets

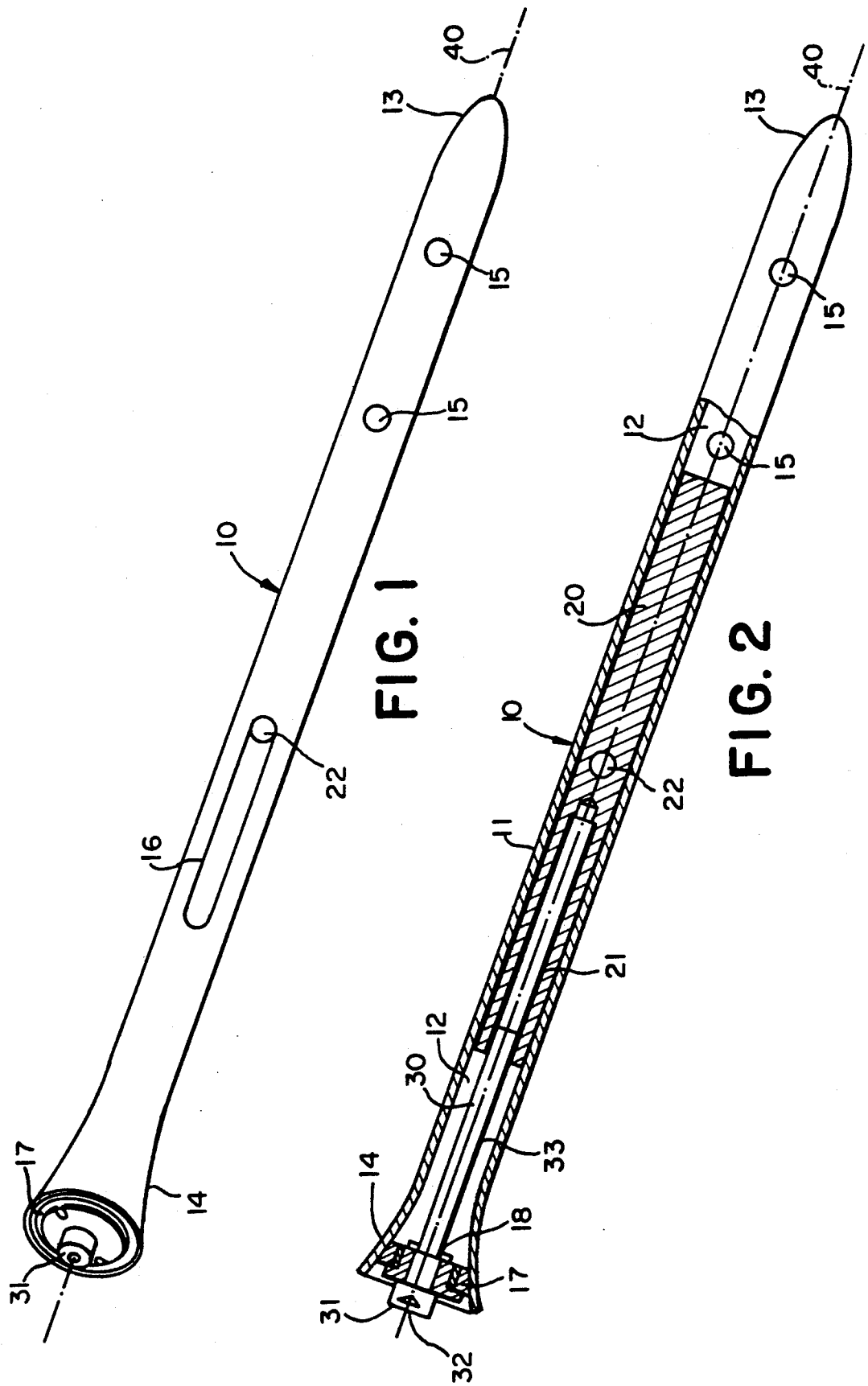

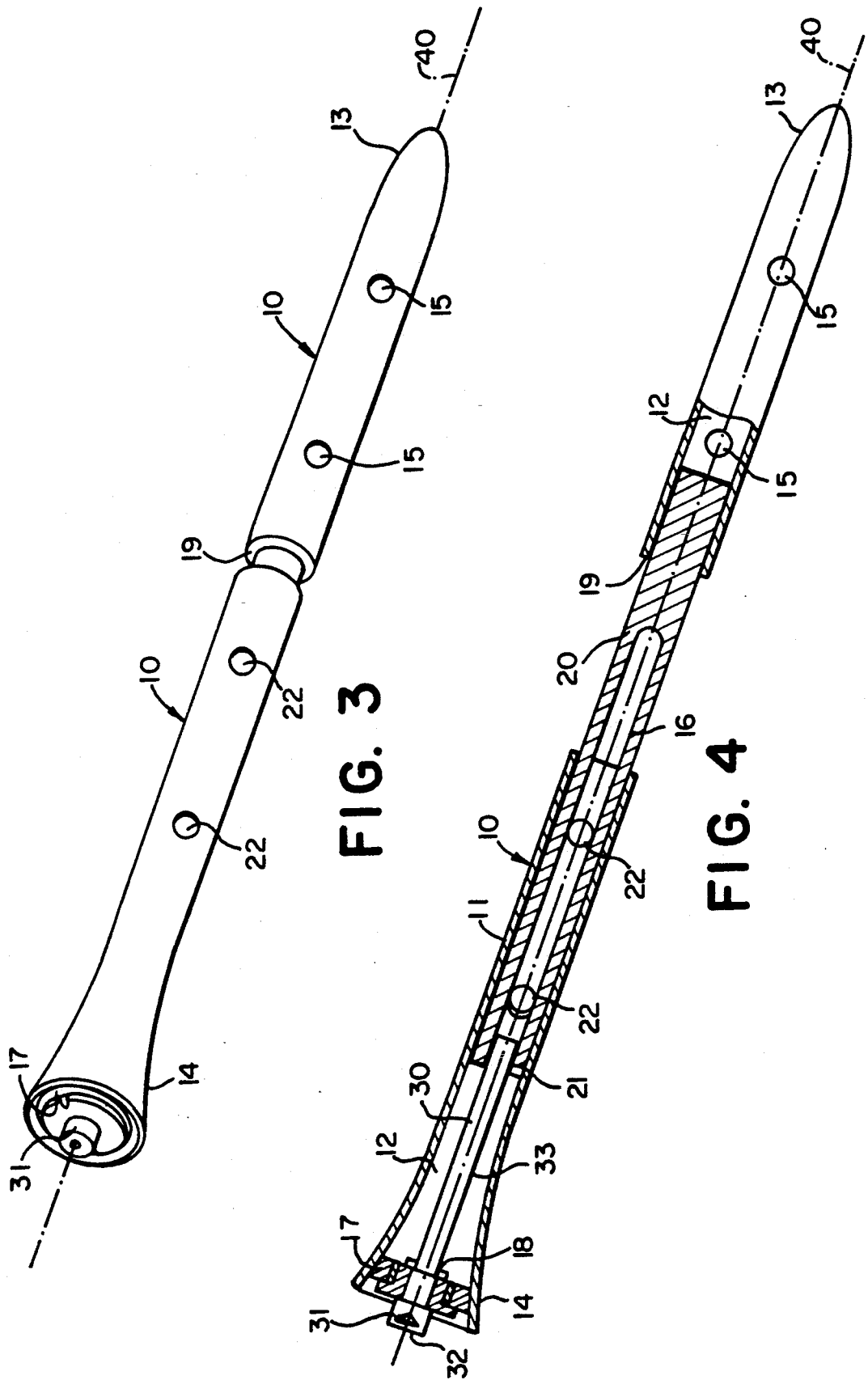

MEDULLARY NAIL

The invention relates to a medullary nail having, forming a cavity, a wall having a tapering end, and having an insertion end and, disposed at intervals over its length, fixing holes which extend transversely through its wall.

It is already known that medullary nailing is used in the field of long tubular bones, following fractures, for settling the two end of the fracture in respect of each other after the fashion of an inner splint. For this, after the medullary cavity has been drilled out, the medullary nail is in most cases rammed home from the proximal end of the medullated bone and, once it is finally positioned, it is secured against axial displacement and twisting by a plurality of transverse bolts which pass through the bone cortex and fixing holes in the medullary nail. Since the periosteum which encloses the outside of the bone is not damaged to any substantial degree with this type of treatment, the nourishment which is important to the healing process is encouraged and infection obviated.

In the advanced stages of fracture healing, the locking pins on one side of the fracture gap can be removed. An axial loading now results in the released part of the bone sliding toward the still pinned bone, which thus produces an axial compression on the fracture gap, so that the newly formed bone becomes solidified.

In the past, lengthening of tubular bones or bridging of defects following shattered breakages, an inflammation of the bone or after the removal of tumours in the region of long tubular bones have been carried out by means of external fixing systems. In such cases, the bone ends are held by bone screws or wires which are passed through the skin and connected on the outside to a frame. By displacing the frame parts associated with the relevant bone ends, by means of tension bolts or wire winches, a relative movement between the bone ends is necessarily achieved, the minimal displacement distances being continuously bridged by newly forming bone tissue. Both for extension and also for segmental displacement, an osteotomy is necessary, and with segmental displacement, the segment of bone which is separated is drawn into the defective zone.

The prior art external fixing systems have an unfavourable force application point so that tilting occurs and expensive patient-impeding structures are needed and they constitute a constant risk of infection due to germs penetrating through the bone screws or the wires and they result in unattractive scars.

The problem on which the invention is based resides then in so modifying a medullary nail that while it maintains its function of serving as an inner splint and providing stability, it does at the same time permit an axial displacement of separate bone parts away from each other.

On a basis of the medullary nail of the type mentioned at the outset, this problem is resolved by an inner part, rotationally rigidly disposed in the cavity and which can be displaced longitudinally by a drive and by, provided in the region of the insertion end, a transversely continuous elongated hole either in the oppositely disposed sides of the wall forming the cavity or in the inner part and by at least one fixing hole aligned with the elongated hole, either in the inner part or in the oppositely disposed sides of the wall forming the cavity.

The drive for longitudinal displacement of the inner part into the cavity may be a mechanical, pneumatic or hydraulic or also an electric, electromagnetic or piezoelectric drive which is installed inside and/or outside the cavity. For example, in the case of a closed cavity, the inner part may take over the function of a piston adapted for longitudinal displacement in the cavity and which in a predetermined manner is subjected to pressure which produces the required displacement. By means of a pneumatic spring, a longitudinal displacement is also possible.

If the inner part is provided with an internally screwthreaded bore extending from one of its ends and if at the insertion end a rod with an external screwthread is rotatably mounted and is in screw-threaded engagement with the internal screwthread in the bore in the inner part, then the rotation of the rod can be accomplished by a rotary drive in the form of a flexible shaft which, after a sufficiently long path through the soft tissue is guided outwardly through the skin and which is provided at its proximal end with a hexagon for rotation. As a rotary drive, it is also possible to use a suitable geared electric motor which is flanged on the proximal end of the medullary nail or which can even be accommodated in the lumen of the medullary nail. The power can be supplied by batteries which are integral with the electric motor or separately by implanting a battery housing into the subcutaneous fatty tissue, a flexible conductor being used for connection. The electric motor can be activated by the application of a magnet by means of a reed contact or in continuous operation.

After drilling out the medullary cavity and applying an osteotomy at a suitable place with an internal saw, the medullary nail constructed according to the invention is driven in and in fact if the elongated hole is disposed in the oppositely disposed portions of the wall of the medullary nail, only sufficiently that it projects from the insertion point by the amount by which the bone is to be lengthened. Once the locking pins have been applied on either side of the osteotomy, then, by longitudinal displacement of the inner part, distraction of the bone ends at the osteotomy site is accomplished.

If the medullary nail is used for a segmental displacement, it may be necessary for the proximal bone portion to be separately secured against axial displacement. To achieve this, there is provision for widening out towards the insertion end the wall which forms the cavity, and in the region of this widening out, strip-forming U-shaped cuts are made, the end connecting portions of which are towards the insertion end of the nail. By means of a wedge element disposed for axial displacement in the cavity and engaging these strips, the strips can be spread apart outwardly and enter into a form-locking connection with the proximal portion of the medullated bone, so that this latter is secured against axial displacements.

In known manner, the cavity in the medullary nail may be wholly or partially open, preferably in the tapering zone but it can however also be completely closed and may have a cylindrical, polygonal or other kind of cross-section, for example a clover leaf cross-section.

Examples of embodiment of the invention will be explained in greater detail hereinafter with reference to the accompanying drawings, in which:

FIG. 1 is a perspective view of a first embodiment of medullary nail;

FIG. 2 is an axial section through the medullary nail in FIG. 1;

FIG. 3 is a perspective view of a second embodiment of medullary nail;

FIG. 4 is an axial section through the medullary nail in FIG. 3;

Figure 5:
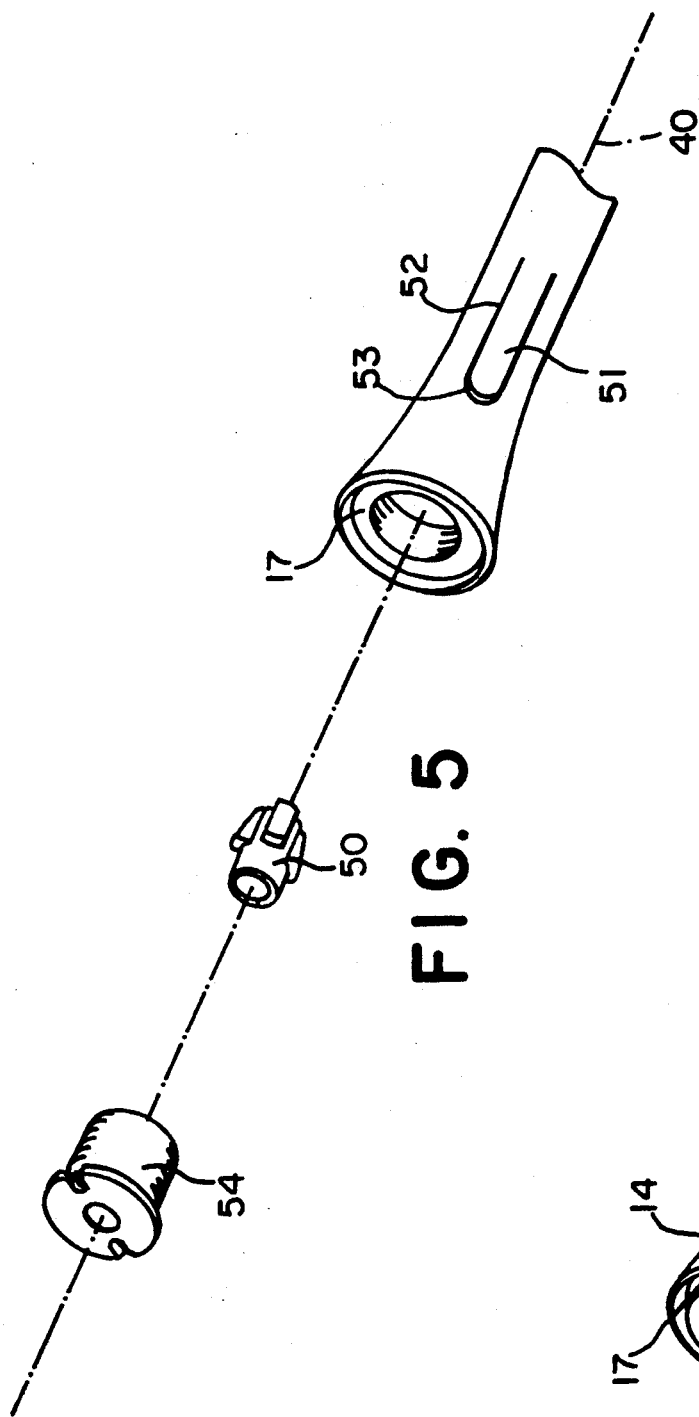
FIG. 5 is an exploded perspective view of the parts of a modified insertion portion of the medullary nail.
Figure 6:
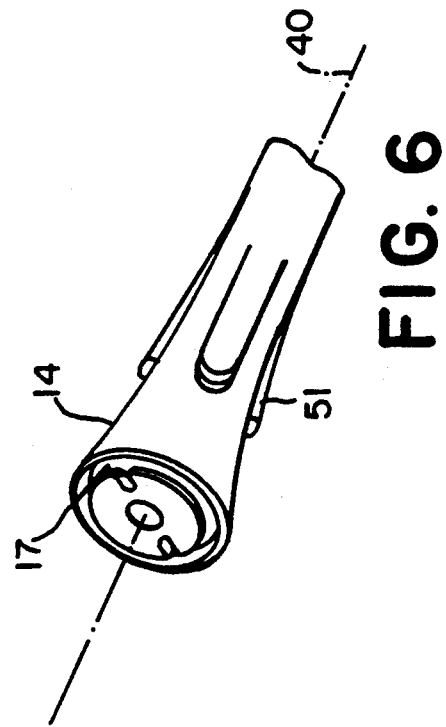
FIG. 6 shows the insertion portion of the medullary nail in FIG. 5 assembled and in an opened-out state.

The medullary nail 10 shown in FIGS. 1 to 6 has, forming a cylindrical cavity 12, a wall 11 of which a widening out insertion end 14 is provided with an inset 17 while its other end 13 tapers to a nail point. The insert 17 has a central bore 18. In the wall 11 of the medullary nail 10 there are in the region of its tapering end 13 spaced apart fixing holes 15 which extend transversely through it.

In the cylindrical cavity 12 of the medullary nail 10 a cylindrical inner part 20 is longitudinally displaceable, secured against rotation and coaxially with the axis 40 of the medullary nail 10. Extending from the end face of the inner part 20 which is towards the widening insertion end 14 there is, coaxially in the inner part 20 a bore 21 with an internal screwthread into which is screwed the external screwthread 33 of a rod 30 which extends through the bore 18 in the insert 17, ending in a head 31 with a recessed hexagonal socket 32. Rotation of the head 31 displaces the inner part 20 axially within the cavity 12 of the medullary nail 10.

Where the embodiment shown in FIGS. 1 and 2 is concerned, there is in the distance from the end of the bore 21 with the internal screwthread a fixing hole 22 which extends transversely through the inner part 20. Aligned with this fixing hole 22 there is in the wall 12 of the medullary nail, on the oppositely disposed sides, an elongated hole 16. The medullary nail 10 in the embodiment shown in FIGS. 1 and 2 is driven in to the extent that proximally it extends from the point of insertion by the amount of bone which is to be lengthened. After application of the locking pins, not shown, through the fixing holes 15, which are disposed on one side of the osteotomy, and through the oppositely disposed elongated holes 16 in the wall 12 of the medullary nail 10 and through the fixing hole 22 on the other side of the osteotomy, by rotation of the head 31 of the rod 30 the edges of the osteotomy are gradually removed from each other, the widening gap which leads to an extension of the bone being filled with newly formed bone tissue.

In the case of the embodiment shown in FIGS. 3 and 4, the wall 12 of the medullary nail 10 is parted at a joint 19 so that the two parts of the medullary nail 10 which are thus formed are displaceable in respect of each other on the inner part 20 in an axially guided manner. With this embodiment, the elongated hole 16 is constructed in the inner part 20 while in the wall 12 of the insertion portion of the medullary nail 10 there are in the longitudinal extension in each case two spaced apart aligned and transversely extending fixing holes 22 on the oppositely disposed sides in the inner part 20, aligned with the elongated hole 16. Where this embodiment is concerned, the medullary nail 10 is rammed completely into the tubular bone without any proximal projection. Then, the locking pins are set, the osteotomy being disposed between the portion with the tapering end 13 and the portion with the widening out insertion end 14 of the medullary nail 10.

In the case of a segmental displacement with an embodiment as shown in FIGS. 1 and 2, in order to secure the proximal bone segment separately against axial displacement, there are constructed in the widening zone of the medullary nail 10 U-shaped incisions 52, the arms of which extend parallel with the axis 40 and the bottom connecting portions 53 of which are towards the insertion end 14. By reason of the U-shaped incisions 52, strips 51 are formed. Guided with external wedges on the rod 10 is a sleeve-like wedge element 50 which, by rotation of a screw 54 maintained in the insert 17 in screw-threaded engagement at the insertion end 14, is axially displaced and by its external wedges, the strips 51 are spread outwardly into the wedging position shown in FIG. 6, so that a positive closure with the proximal bone ends is achieved, together with a securing of its position.

We claim:

1. A medullary nail, comprising
   a wall forming a cavity which has a tapering distal end and a proximal driving-in end,
   spaced fixing holes extending transversely through the wall over its length,
   an inner part disposed in the cavity without being able to rotate, which has an opening associated with at least one of the fixing holes extending transversely therethrough,
   a rod acting on the inner part with an external thread for a longitudinal displacement of the inner part and the wall upon rotation of the rod, altering the distance between the fixing holes,
   an insert (17) with a central bore (18) mounted at the opening of the driving-in end of the cavity,
   said rod (30) being rotatably mounted and extending through the central bore (18), and
   an external thread formed on the rod (30) and being in screw-threaded engagement with an internal thread provided in a coaxial bore (21) in the inner part (20),
   wherein the parts of a bone secured to the wall (11) on the one side, and the inner part (20), on the other side, gradually become separable from each other while forming a widening gap which becomes filled with new bone tissue.

2. The medullary nail of claim 1, wherein the inner part (20) is longitudinally displaced into the cavity (12) and adapted to be driven by a mechanical, pneumatic, hydraulic, electric, electromagnetic, or piezoelectric drive located within or outside the cavity.

3. The medullary nail of claim 2, wherein the wall (11) forming the cavity (12) is divided longitudinally by a separating groove (19), and the two sections of the wall (11) thus formed are axially guided and displaceably mounted on the inner part (20) and are provided with fixing holes (15, 22), and the opening extending transversely through the inner part (20) is an elongated hole (16).

4. The medullary nail of claim 3, further including
   strips formed by U-shaped cuts made in the driving-in end of the wall, and
   wedge means housed in the cavity for wedging the strips outwardly.

5. The medullary nail of claim 2, wherein one of the fixing holes in the wall (11) associated with the opening (22) of the inner part (20) is an elongated hole (16).

6. The medullary nail of claim 1, wherein the wall (11) forming said cavity (12) is divided in a longitudinal direction by a separating groove (19) into a first section and a second section, the first section and the second section of the wall (11) are axially guided and displaceably mounted on the inner part (20) and are provided with fixing holes, and the opening extending transversely through the inner part (20) is an elongated hole (16).

7. The medullary nail of claim 1, wherein one of the fixing holes in the wall (11) associated with the opening (22) of the inner part (20) is an elongated hole (16).

8. The medullary nail of claim 1, further including
strips formed by U-shaped cuts made in the driving-in end of the wall, and
wedge means housed in the cavity for wedging the strips outwardly.

* * * * *